United States Patent
Beerthuis et al.

(10) Patent No.: US 11,613,505 B2
(45) Date of Patent: Mar. 28, 2023

(54) SELECTIVE HYDROGENATION OF POLYUNSATURATES

(71) Applicant: BP P.L.C., London (GB)

(72) Inventors: Rolf Beerthuis, Utrecht (NL); Krijn De Jong, Utrecht (NL); Petra De Jongh, Utrecht (NL); John Glenn Sunley, Hull (GB)

(73) Assignee: BP P.L.C., London (GB)

( * ) Notice: Subject to any disclaimer, the term of this patent is extended or adjusted under 35 U.S.C. 154(b) by 3 days.

(21) Appl. No.: 16/972,996

(22) PCT Filed: Jun. 3, 2019

(86) PCT No.: PCT/EP2019/064378
§ 371 (c)(1),
(2) Date: Dec. 7, 2020

(87) PCT Pub. No.: WO2019/233961
PCT Pub. Date: Dec. 12, 2019

(65) Prior Publication Data
US 2021/0253496 A1  Aug. 19, 2021

(30) Foreign Application Priority Data
Jun. 7, 2018 (EP) .................... 18176645

(51) Int. Cl.
| | | |
|---|---|---|
| C07C 5/09 | (2006.01) | |
| B01J 21/18 | (2006.01) | |
| B01J 23/72 | (2006.01) | |
| B01J 35/00 | (2006.01) | |
| B01J 35/02 | (2006.01) | |
| B01J 37/02 | (2006.01) | |
| B01J 37/08 | (2006.01) | |
| B01J 37/16 | (2006.01) | |

(52) U.S. Cl.
CPC .............. *C07C 5/09* (2013.01); *B01J 21/18* (2013.01); *B01J 23/72* (2013.01); *B01J 35/006* (2013.01); *B01J 35/023* (2013.01); *B01J 37/0201* (2013.01); *B01J 37/08* (2013.01); *B01J 37/16* (2013.01); *C07C 2521/18* (2013.01); *C07C 2523/72* (2013.01)

(58) Field of Classification Search
CPC ......... C07C 5/05; C07C 5/09; C07C 2521/18; C07C 2523/72; B01J 21/18; B01J 23/72; B01J 35/0013; B01J 35/006; B01J 35/023; B01J 37/0201; B01J 37/08; B01J 37/16

See application file for complete search history.

(56) References Cited

U.S. PATENT DOCUMENTS

| | | | |
|---|---|---|---|
| 2,964,579 A | 12/1960 | William et al. | |
| 3,481,999 A | 12/1969 | Reich | |
| 4,189,599 A * | 2/1980 | Kesling, Jr. ............. | C07C 69/44 560/190 |
| 4,440,956 A | 4/1984 | Couvillion | |
| 6,054,409 A | 4/2000 | Thanh et al. | |
| 2003/0036669 A1 | 2/2003 | Ryu et al. | |
| 2007/0123738 A1* | 5/2007 | Tokuyasu ................ | C07C 7/163 585/16 |
| 2012/0071700 A1* | 3/2012 | Huang ................. | B01J 35/1038 502/158 |
| 2015/0166475 A1* | 6/2015 | Peitz ..................... | C07C 319/18 568/59 |

FOREIGN PATENT DOCUMENTS

EP  0908235 A2  4/1999

OTHER PUBLICATIONS

Merabti et al. "Synthesis and characterization of activated carbon-supported copper or nickel and their catalytic behavior towards benzaldehyde hydrogenation." Reaction Kinetics, Mechanisms and Catalysis. 2010, vol. 10(1), p. 195-208.
Din et al. "Synthesis, characterization and activity pattern of carbon nanofibers based copper/zirconia catalysts for carbon dioxide hydrogenation to methanol: Influence of calcination temperature." Journal of Power Sources. 2014, vol. 274, p. 619-628.
Dandekar et al. "Carbon-Supported Copper Catalysts—II. Crotonaldehyde Hydrogenation." Journal of Catalysis. 1999, vol. 184(2), p. 421-439.
Rao et al. "Furfural hydrogenation over carbon-supported copper." Catalysis Letters. 1999, vol. 69, p. 51-57.
Munnik et al. "Recent Developments in the Synthesis of Support Catalysts." Chemical Reviews. 2015, vol. 115, p. 6687-6718.
Bender. "An Overview of Industrial Processes for the Production of Olefins—C4 Hydrocarbons." ChemBioEng Reviews. 2014, vol. 1, p. 136-147.
International Search Report and Written Opinion of International Application No. PCT/EP2019/064378 dated Oct. 24, 2019.

* cited by examiner

*Primary Examiner* — Youngsul Jeong
*Assistant Examiner* — Jason Y Chong
(74) *Attorney, Agent, or Firm* — McDonnell Boehnen Hulbert & Berghoff LLP

(57) ABSTRACT

The present invention provides a process for the hydrogenation of polyunsaturated hydrocarbon compounds, in particular di-olefins and alkynes, more particularly di-olefins, said process comprising contacting a feed comprising one or more polyunsaturated hydrocarbon compounds with a catalyst comprising copper and carbon in the presence of hydrogen, preferably wherein the catalyst is a copper catalyst on a carbon-containing support. The present invention also provides a process for producing a copper catalyst on a carbon-containing support and the use of a copper catalyst on a carbon-containing support to increase the selectivity towards di-olefin hydrogenation over mono-olefin hydrogenation in a process for hydrogenation of one or more di-olefins.

12 Claims, No Drawings

SELECTIVE HYDROGENATION OF POLYUNSATURATES

This application is a national stage application under 35 U.S.C. § 371 of International Application No. PCT/EP2019/064378, filed Jun. 3, 2019, which claims priority to European Application No. 18176645.2, filed Jun. 7, 2018, the disclosures of which are explicitly incorporated by reference herein.

The present invention relates to a catalyst comprising copper and carbon and the use thereof in a process for the selective hydrogenation of polyunsatured compounds, for example di-olefins and alkynes, as well as a method of preparing the catalyst and uses of the same. In a particular embodiment, the invention relates to the selective hydrogenation of di-olefins, such as butadiene, optionally in the presence of excess mono-olefins, such as propylene, butylene and/or ethylene, by employing a copper catalyst on a carbon-containing support.

Selective hydrogenation of components of a mixture is desirable in the production of purified feedstocks for numerous chemical processes. Examples of where this may be useful is in the separation of products obtained by the thermal or catalytic cracking of hydrocarbons or hydrocarbon coking operations where fractions are produced that consist of a mixture of hydrocarbons, for example $C_4$ hydrocarbons. Further fractionation results in fractions consisting of butylenes, butane and small quantities of 1,3-butadiene, the latter interfering with the useful application of the former. In another example, undesirable di-olefin impurities may be found in mono-olefin streams produced by the dehydrogenation of an alkane, such as a butylene rich stream comprising 1,3-butadiene impurities formed following dehydrogenation of butane.

In many instances, it is desirable to preserve or to increase the purity of mono-olefin streams, for the purpose of subsequent processing, particularly in the case of polymerization reactions. For instance, it is undesirable for 1-butylene streams commonly used in the synthesis of "butyl" rubber to possess more than 1% of di-olefins. Similarly, other mono-olefin feed streams are negatively impacted by contamination with di-olefins.

Numerous efforts have been made in the purification of mono-olefin streams for the benefit of downstream processing. For instance, in the removal of alkyne and di-olefin impurities from mono-olefin streams, certain supported palladium and copper catalysts have been employed. Palladium catalysts have been found to have excellent activity but can suffer from lower selectivity for alkynes over di-olefins and mono-olefins in comparison to copper alternatives and rapid deactivation, without being bound by theory, it is believed that such deactivation is caused by the deposition of carbonaceous by-products on the catalyst. In order to improve the selectivity and stability, silver or gold have been added to palladium catalysts as modifiers. For example, U.S. Pat. No. 6,054,409 discloses a $PdAg/Al_2O_3$ catalyst used to remove acetylene in ethylene, with only minor loss of ethylene over long processing times. However, the addition of dopant metals can also negatively impact catalyst activity.

Certain copper-based catalysts, in particular those comprising silica, alumina or titania supports, have been identified as highly selective catalysts for the selective hydrogenation of alkynes in feeds containing di-olefins and mono-olefins. Stronger adsorption of acetylene than ethylene functional groups on copper surfaces has been proposed as being crucial for the selective partial hydrogenation. However, copper catalysts have demonstrated low activity in comparison to palladium alternatives historically.

In order to improve the activity of copper catalysts in selective hydrogenation reactions, further metals have been included in the catalyst, which act as promoters. For example, U.S. Pat. No. 4,440,956 discloses the removal of acetylenes from hydrocarbon streams, without loss of di-olefinic unsaturation, using a copper catalyst supported on a special grade of gamma alumina and activated by at least one metal selected from silver, platinum, palladium, manganese, cobalt, nickel, chromium and molybdenum. These catalysts were found to reach lower acetylene levels with less di-olefin loss than previously possible.

Examples of di-olefin removal in the presence of mono-olefins include the use of a $CuNiCr/SiO_2$ and CuNiMg/pumice catalysts, as disclosed in U.S. Pat. No. 3,481,999, in the selective hydrogenation of 1,3-butadiene in the presence of 1-butylene, with little change in the activity and selectivity of the catalyst even after 150 and 200 days of operation, respectively.

U.S. Pat. No. 2,964,579 discloses a $CuCr_2O_2/Al_2O_3$ catalyst which was found to selectively reduce butadienes in the presence of butylenes and butanes at low temperatures. It was found that after about 40 hours of continuous operation, the activity of the catalyst declined significantly. The activity and selectivity could nevertheless be maintained over long operating periods of several months or more by periodically purging the catalyst with hydrogen.

Further additives have been used in promoted copper hydrogenation catalysts in order to improve their properties. For example, it has been found that copper catalysts used in hydrogenation reactions can exhibit short cycle time due to polymer deposition on the catalyst surface. This can be particularly prevalent in feeds with high alkyne concentrations or when the catalyst is used continuously without purging. US 2003/0036669 discloses the selective hydrogenation of acetylenic compounds in olefin streams, which may include 1,3-butadiene, using copper catalysts promoted by a Group VIII metal such as palladium, ruthenium or nickel supported on alumina. It was found that by further modifying the catalyst with silver and/or gold, polymer formation was reduced, the yield of desired olefins was improved and the loss of copper and promoter metal caused by leaching was prevented. The addition of zinc oxide was also shown to improve the catalyst activity, the yield of olefins, the catalyst cycle time and reduce the loss of copper and palladium due to leaching.

High performance over time is a key aspect in the implementation of industrial catalysts. Previous examples of various copper-catalysed selective hydrogenation reactions all suffer from activity/deactivation issues which must be accommodated, for instance by onerous purging steps or by using modifiers/promoters. There remains a need in the art for catalysts capable of hydrogenating polyunsaturated hydrocarbon compounds, such as di-olefins and alkynes, particularly with a high selectively over the hydrogenation of mono-olefins that may also be present, and which are stable over long periods of operation.

The present invention is based on the surprising discovery that high catalyst stability over prolonged operation times and high selectivity for the hydrogenation of polyunsaturated hydrocarbon compounds, for example di-olefin hydrogenation over mono-olefin hydrogenation, can be achieved using a catalyst comprising copper and carbon, such as a copper on a carbon-containing support. Furthermore, it has been found that such copper and carbon-containing catalysts exhibit very good selectivity towards hydrogenation of di-olefins, such as 1,3-butadiene, over mono-olefins, which selectively surprisingly increases with increasing time-on-stream. Further still, the catalysts can also be used effectively without requiring the presence of a promoter metal and exhibit superior stability and lifetime in comparison to conventional copper hydrogenation catalysts, without the need of additional purging steps.

Thus, in a first aspect, the present invention provides a process for the hydrogenation of polyunsaturated hydrocarbon compounds, in particular di-olefins and alkynes, more particularly di-olefins, said process comprising contacting a feed comprising one or more polyunsaturated hydrocarbon compounds with a catalyst comprising copper and carbon in the presence of hydrogen, preferably wherein the catalyst is a copper catalyst on a carbon-containing support.

In another aspect, the present invention provides a process for producing a copper catalyst on a carbon-containing support, the process comprising the steps of:

(a) impregnating a carbon-containing support with one or more compounds containing copper; and (b) heating the impregnated support from (a) under a non-reducing atmosphere to decompose the compound containing copper;

(c) optionally, treating the support from (b) under a non-reducing atmosphere, such as under an oxygen-containing stream; and (d) reducing the metal on the support at a temperature of from 100° C. to 500° C.

In a yet further aspect, the present invention provides the use of a copper catalyst on a carbon-containing support to increase the selectivity towards di-olefin hydrogenation over mono-olefin hydrogenation in a process for hydrogenation of one or more di-olefins.

In a yet further aspect, the present invention provides a process for the hydrogenation of polyunsaturated hydrocarbon compounds, said process comprising contacting a feed comprising one or more polyunsaturated hydrocarbon compounds with a catalyst comprising copper and carbon in the presence of hydrogen. In a preferred embodiment, the polyunsaturated hydrocarbon compounds are selected from di-olefins, alkynes, and mixtures thereof; in a particularly preferred embodiment, the present invention provides a process for the hydrogenation of di-olefins.

In the present invention, the term "polyunsaturated hydrocarbon compounds" and the like means hydrocarbon compounds that contain: at least one alkyne bond; two or more olefinic bonds; or, a combination of at least one alkyne bond and at least one olefinic bond. In the present invention, the term "di-olefin", "di-olefinic hydrocarbon compound", and the like, mean hydrocarbon compounds that contain two olefinic bonds. In the present invention, the term "alkyne", "alkynic hydrocarbon compound", and the like, mean hydrocarbon compounds that contain at least one alkyne bond. In the present invention, the term "mono-olefin", "mono-olefinic hydrocarbon compound", and the like, mean hydrocarbon compounds that contain one olefinic bond. For the purposes of the present invention, the presence of an aromatic ring will not be considered as contributing to the unsaturation of the hydrocarbon compound, however, unsaturation present on any groups attached to an aromatic ring would contribute to the unsaturation of the hydrocarbon compound; for example, styrene would be considered as a mono-olefin, and phenylacetylene would be considered as an alkyne.

In the present invention, when the feed comprising one or more polyunsaturated hydrocarbon compounds comprises di-olefins, the di-olefins may be conjugated or unconjugated, and the presence of conjugated di-olefins will generally vary depending on the length of the carbon chains present in the polyunsaturated compounds. In a particular embodiment, the di-olefins comprise or consist of 1,3-di-olefins.

Preferably, the feed will comprise at least two unsaturated hydrocarbon compounds, wherein at least one of the unsaturated hydrocarbon compounds is a polyunsaturated hydrocarbon compound. For example, the feed can comprise at least two unsaturated hydrocarbon compounds, wherein at least one is a polyunsaturated hydrocarbon compound and at least one is a mono-olefinic compound. Alternatively, the feed can comprise at least two different polyunsaturated hydrocarbon compounds, for example at least one di-olefinic hydrocarbon compound and at least one alkynic hydrocarbon compound.

Without limiting the scope of the catalyst or process, in some embodiments, the feed comprising one or more polyunsaturated hydrocarbon compounds comprises at least one mono-olefin and at least one di-olefin. In other embodiments, the feed comprising one or more polyunsaturated hydrocarbon compounds comprises at least one mono-olefin and at least one alkyne. In other embodiments, the feed comprising one or more polyunsaturated hydrocarbon compounds comprises at least one di-olefin and at least one alkyne.

The feed comprising one or more polyunsaturated hydrocarbon compounds will typically comprise primarily of hydrocarbon compounds having from 2 to 16 carbon atoms. In some or all embodiments, the feed comprising one or more polyunsaturated hydrocarbon compounds will consist essentially of hydrocarbon compounds having from 2 to 16 carbon atoms. In some or all embodiments, the feed comprising one or more polyunsaturated hydrocarbon compounds will consist essentially of hydrocarbon compounds having from 2 to 10 carbon atoms. In some or all embodiments, the feed comprising one or more polyunsaturated hydrocarbon compounds will consist essentially of hydrocarbon compounds having from 2 to 8 carbon atoms. In some or all embodiments, the feed comprising one or more polyunsaturated hydrocarbon compounds will consist essentially of hydrocarbon compounds having from 2 to 6 carbon atoms. In some or all embodiments, the feed comprising one or more polyunsaturated hydrocarbon compounds will consist essentially of hydrocarbon compounds having from 2 to 4 carbon atoms.

An advantage of the present invention is the ability for achieving a particularly high level of selectivity for the hydrogenation of polyunsaturated hydrocarbon compounds over mono-olefinic compounds. This process of the present invention may therefore be deployed as part of a process for reducing the content of di-olefins in a mono-olefin stream, or for reducing the content of alkynes in a mono-olefin stream, or for reducing the content of di-olefins and alkynes in a mono-olefin stream. Whilst not wishing to be bound by theory, compounds containing alkyne compounds may be more susceptible to hydrogenation to mono-olefins compared to the hydrogenation of di-olefins to mono-olefins, and that di-olefins are may be more susceptible to hydrogenation to mono-olefins compared to the hydrogenation of mono-olefins to alkanes; thus, the process of the present invention may be deployed as part of a process for reducing the content of alkynes in a mono-olefin stream, or for reducing the content of alkynes and di-olefins in a mono-olefin stream, or for reducing the content of alkynes in a di-olefin stream.

Non-limiting examples of feed compositions to the process of the present invention include butene compositions comprising butadiene(s) and/or butyne(s); propylene compositions comprising propyne; ethylene compositions comprising acetylene; styrene compositions comprising phenylacetylene; and, butadiene compositions comprising butyne(s). In a particular embodiment, the feed comprises 1-butene, 1,3-butadiene, and 1-butyne.

Where mono-olefins are present in the feed comprising polyunsaturated hydrocarbon compounds, the proportion of polyunsaturated hydrocarbon compounds in the feed relative to mono-olefins is not particularly limited. However, a particular benefit of the invention is to reduce the level of di-olefins as a contaminant of a mono-olefin stream; therefore, in some or all embodiments, the proportion of di-olefins in the feed relative to mono-olefins is less than 25% v/v, typically less than 10% v/v, preferably less than 5% v/v, for example less than 1% v/v, and will typically be above 0.001% v/v, for example above 0.01% v/v, or even above 0.1% v/v.

In some or all embodiments, the process of the present invention comprises contacting one or more di-olefins with the catalyst comprising copper and carbon in the presence of hydrogen, wherein the one or more di-olefins are contained in a feed also comprising one or more mono-olefins.

The catalyst for the selective hydrogenation of the present invention comprises copper and carbon.

Preferably, the catalyst comprises copper on a carbon-containing support material. In some or all embodiments of the present invention, the catalyst comprises copper on a carbon-based support. The inclusion of carbon in the copper catalyst, in particular the use of a carbon-containing support in the catalyst, has been found to confer particularly desirable properties on the copper catalyst in terms of its selectivity for the hydrogenation of polyunsaturates, such as di-olefins. Remarkable long-term stability has also been observed with such supported catalysts used in accordance with the present invention; without being bound by any particular theory, the long term stability of the supported catalyst is believed to be the result of a high resistance towards coking. Moreover, the catalyst structure has been found to be relatively stable under typical reaction conditions using such copper catalysts supported on a carbon-containing support.

In some or all embodiments, the catalyst is a catalyst comprises copper on a carbon-based support, and said catalyst may additionally comprise one or more modifiers, promoters, dispersion aids or binders.

In some or all embodiments, the catalyst comprises copper in combination with one or more other metallic promoters or modifiers. In some or all embodiments, the catalyst may additionally comprise one or more transition metals, such as silver, gold, zinc, manganese, chromium or mixtures thereof, either in their metallic form or in the form of oxides. In some or all embodiments, the catalyst may comprise an alkali metal, an alkaline earth metal, or mixtures thereof, non-limiting examples include potassium or sodium. In some or all embodiments, the catalyst may comprise one or more other metallic promoters or modifiers selected from silver, gold, manganese, chromium, potassium and sodium, or mixtures thereof, either in their metallic form or in the form of oxides.

In some or all embodiments, the total metal content of the catalyst, including copper and any metallic promoters and/or modifiers which may be present, is from 0.05 to 50 wt %, such as from 0.1 to 40 wt %, for example 0.5 to 30 wt %, on an elemental basis, based upon the total weight of the catalyst.

In some or all embodiments, the catalyst is supported on a carbon-containing support and comprises copper in an amount of from 0.05 to 50 wt %, preferably in the range of from 0.05 to 30 wt. %, such as from 0.5 to 20 wt %, for example 1 to 15 wt. %, on an elemental basis, based on the total weight of the catalyst.

In embodiments where modifiers and promoters are present, these may be present in an amount of from 0.05 to 25 wt %, such as from 0.1 to 15 wt. %, for example from 0.5 to 10 wt %, on an elemental basis, based on the total weight of the catalyst.

The supported catalysts may be prepared by any suitable method known in the art. For example, such catalysts may be prepared by impregnation, precipitation or gelation, preferably by impregnation. A suitable impregnation method, for example, comprises impregnating a carbon-containing support material with a compound of copper which is thermally decomposable to the oxide form. Any suitable impregnation technique including the incipient wetness technique or the excess solution technique, both of which are well-known in the art, may be employed. The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation.

The solvent for the impregnation solution may suitably be an aqueous solution, an organic solution, or a mixture of aqueous and organic solvent(s), depending upon the solubility of the copper compound being used; examples of suitable organic solvents may include, for example, alcohols, ketones, liquid paraffinic hydrocarbons and ethers, and suitable aqueous-organic solvents may include aqueous alcoholic solutions. The copper compound used is typically a thermally decomposable copper compound. Various copper compounds and copper salts which are thermally decomposable such that they will form metallic copper or copper oxides, or a mixture thereof on the support material are well known in the art. Non-limiting examples of thermally decomposable copper salts which may be used include chloride, nitrate, sulphate, oxalates, and acetate salts of copper or organic complexes of copper.

Acid additives may also be included in the impregnating solution, such as nitric acid. The impregnation solution may thus have an acidic pH, preferably a pH less than pH 2, for example about pH 1.

In some or all embodiments of the present invention, the catalyst is a copper catalyst supported on a carbon-containing support, namely a support material which comprises carbon, for example carbon nitride. Preferably, the carbon-containing support material is a carbon-based support, namely a support material which comprises carbon as a major element. Suitable examples of carbon-based supports include, but are not limited to, graphite, graphene, carbon aerogels, carbon nanotubes and carbon nanofibers and carbon nanoplatelets, polymeric materials, carbon black, turbostratic carbon, and activated carbon. Other suitable carbon-containing supports and carbon-based supports are well known in the art. Preferably, the carbon-containing support has a high specific surface area and a significant pore volume.

The carbon-containing support may be in the form of a powder, granulate or a shaped particle. The term "shaped particle" is intended to mean a shaped support (for instance, by extrusion), examples of suitable shapes which such shaped particles may have include cylinders, spheres, dilobes, trilobes, quadrolobes, hollow cylinders, Berl saddles, Pall rings, and the like. The formation of shaped particles is well known in the art. When the carbon-containing support is in the form of a shaped particle, the impregnation of the carbon-containing support may be performed on the shaped particle, or it may be performed on the powder, which may then subsequently be formed into the shaped particle after impregnation.

In some embodiments, the carbon-based support has a BET surface area of at least 100 $m^2$ $g^{-1}$, preferably at least 200 $m^2$ $g^{-1}$, more preferably at least 300 $m^2$ $g^{-1}$, for example at least 400 $m^2$ $g^{-1}$.

The pore volume of the support is typically more than 0.1 mL $g^{-1}$, more typically more than 0.2 m L $g^{-1}$, preferably more than 0.5 m L $g^{-1}$, such as more than 0.8 m L $g^{-1}$. The average pore radius (prior to impregnation) of the support material is 1 to 1000 nm, preferably 1 to 500 nm, more preferably 1.5 to 100 nm, such as 2.0 to 50 nm.

The surface area, pore volume, pore size distribution and average pore radius of the carbon-containing support may be determined from physisorption using nitrogen or argon, mercury porosimetry, or other methods known in the art. A procedure which may be used is an application of British Standard methods BS4359: Part 1:1984 'Recommendations for gas adsorption (BET) methods' and BS7591:Part 2:1992, 'Porosity and pore size distribution of materials'—Method of evaluation by gas adsorption. The resulting data may be reduced using the BET method (over the pressure range 0.05-0.20 $P/P_o$) and the Barrett, Joyner & Halenda (BJH) method (for pore diameters of 2-100 nm) to yield the surface area and pore size distribution respectively. Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380.

Without being bound by theory, it is believed that the presence of defects or of heteroatoms, such as oxygen, nitrogen or hydrogen, and/or boron-containing groups, in the carbon-containing support may improve the synthesis and/or the stability of small copper particles on the surface of the support. Heteroatoms and/or defects may be native to the carbon-containing support, in which case no further treatment may be necessary or desired.

However, heteroatoms and/or defects may be introduced in the carbon-containing support, or increased in number/density, by treatment with a solid, liquid or gas-phase oxidant, suitable oxidants are known in the art, non-limiting examples include air, ozone, $H_2O_2$, $KMnO_4$, $H_2SO_4$, $HNO_3$, and mixtures of acids. Without being bound by theory, it is believed that such a treatment of the carbon-containing support increases the density of oxygen-containing surface groups and/or defects in the carbon-containing support, and enhances the interaction of the copper precursor with the carbon-containing support during impregnation, facilitating copper dispersion over the support. As a result, treatment of the carbon support with a solid, liquid or gas-phase oxidant prior to impregnation may result in a high copper dispersion upon impregnation.

In an optional embodiment, the carbon-containing support is treated with an acid solution, for example nitric acid, before impregnating the support with copper. In some or all of the optional embodiments, the carbon-containing support is treated with nitric acid at a temperature in the range of from room temperature to 250° C., preferably at elevated temperature, typically at a temperature in the range of from 50° C. to 150° C., preferably from 70° C. to 120° C., and for a time sufficient to introduce oxygen groups and defects to the carbon, typically in the range of from 1 minute to 24 hours, for example from 10 minutes to 5 hours, for example from 10 to 120 minutes, in order to obtain an oxidised carbon-containing support.

The volume of impregnation solution added to the support during the impregnation is used is not restricted, and hence may be enough to achieve incipient wetness or excess solution impregnation. The impregnation solution has a metal concentration appropriate to achieve the desired loading. For example, the copper concentration is selected and adjusted to obtain the desired copper weight loading. Preferably, incipient wetness impregnation is used as this preparation technique allows for precise control over the composition of the catalysts as the final metal weight loading corresponds directly to the nominal amount of added metal, as described in P. Munnik et al., *Chemical Reviews* 2015, 115, 6687-6718. In particularly preferred embodiments, impregnation is performed by incipient wetness impregnation using a copper nitrate solution on an oxidised carbon-containing support.

The impregnated support may be dried using any conventional technique, including heating and/or placing the sample under vacuum, preferably by heating. On a commercial scale, drying may be achieved by a purge of hot inert gas, such as nitrogen or air.

The impregnated support is then be heated under non-reducing atmosphere in order to thermally decompose the copper-containing compound. Any suitable temperature may be used which achieves thermal decomposition of the copper containing compound without negatively impacting upon the physical characteristics of the support. In some or all embodiments, the impregnated support is heated at a temperature in the range of from 100° C. to 700° C., for example in the range of from 100° C. to 400° C., or in the range of from 150° C. to 300° C., such as from 200° C. to 250° C. The sample may be heated for a time period sufficient to decompose the copper compound to metallic copper or a copper oxide, or a mixture thereof, the actual amount of time required will vary depending upon the copper compound used, the support and the temperature applied, but may be from 10 min to 5 hours, such as from 30 to 90 minutes. The sample may be heated under a flow of inert gas, for example nitrogen, helium or argon, preferably nitrogen.

The impregnated support may optionally then be treated under a non-reducing atmosphere, such as under an oxygen-containing atmosphere, at a temperature equal to or greater than ambient temperature, preferably at an elevated temperature; without wishing to be bound by theory, this optional treatment is believed to help achieve a suitable particle size and highly-dispersed copper particles on the support and/or passivate the copper deposited on the support. The non-reducing atmosphere is preferably an oxygen-containing atmosphere, such an oxygen-containing atmosphere may comprise an inert diluent gas, e.g. nitrogen; the oxygen-containing atmosphere may suitably comprise from 15 to 25% v/v oxygen, the balance preferably being made up of an inert diluent gas. In a particular embodiment, the oxygen-containing atmosphere is air.

The treatment under a non-reducing atmosphere may conveniently be achieved by treating the impregnated support under a stream of non-reducing gas, for example under an oxygen-containing stream, at elevated temperature, such as from 30° C. to 800° C., preferably in the range of from 50° C. to 450° C.

The copper on the support is subsequently reduced to obtain the active catalyst prior to use. The reduction of the copper catalyst may conveniently be performed in the reactor by any suitable methods of reducing copper catalysts known in the art. One such suitable method of reducing the copper catalyst is reducing the catalyst under a hydrogen-containing gas at an elevated temperature.

In some or all embodiments, the catalyst is reduced under a flow of a hydrogen-containing gas at a temperature in the range of from 100° C. to 450° C., temperatures of reduction may be from 250° C. to 450° C., from 350° C. to 450° C., or from 375° C. to 425° C., such about 400° C., or lower temperatures may be used, such as less than 200° C.

In embodiments where hydrogen-containing gas is used for reduction, this may be pure hydrogen or a mixture of hydrogen with an inert diluent gas, for example nitrogen, in concentrations in the range of from 1 to 80 vol. % of hydrogen, such as 2 to 50 vol. %, for example 2 to 20 vol. %, or 2 to 10 vol. %, or even 4 to 6 vol. % hydrogen.

In another aspect, the present invention provides a process for producing a copper catalyst on a carbon-containing support, the process comprising the steps of:

(a) impregnating a carbon-containing support with one or more compounds containing copper; and (b) heating the impregnated support from (a) under a non-reducing atmosphere to decompose the compound containing copper;

(c) optionally, treating the support from (b) under a non-reducing atmosphere, such as under an oxygen-containing stream; and (d) reducing the metal on the support at a temperature of from 100° C. to 500° C.

In the embodiments for the hydrogenation of di-olefins, the catalyst is obtainable, preferably obtained, from the above preparation process comprising steps (a) to (d).

Whilst not wishing to be bound by theory, following impregnation and reduction, it is believed that $Cu^0$ particles are formed on the carbon-containing support which may be made up of one or more crystallites (corresponding to single-crystal grains having a single crystalline phase). The size and distribution of the copper crystallites may suitably be determined by X-ray diffraction (XRD), whilst the surface-averaged particle size of the Cu (oxide) particles may suitably be determined by transmission electron microscopy (TEM), high angle annular dark field scanning transmission electron microscopy (HAADF-STEM) X-ray photoelectron spectroscopy, chemisorption using hydrogen or nitrous oxide, or other methods known in the art.

Using the above preferred method for preparing the supported catalyst, it is has been found to be possible to control the particle so as to be below 25 nm, or even below 10 nm. Thus, in some or all embodiments, the surface-averaged particle size of the copper particles on the support is less than 25 nm, preferably below 20 nm, and may conveniently be below 10 nm. In some embodiments, the surface-averaged particle size of the copper particles on the support may be less than 1 nm. Whilst not wishing to be bound by theory, it is not believed that for particles having sizes of 10 nm or less, catalyst selectivity is largely not an effect of particle size down to sizes of approximately 0.5 nm. By also using carbon as the catalyst support, catalyst deactivation can be substantially abated. Thus, in some or all embodiments, the surface-averaged particle size of the copper particles on the support is in the range of from 0.5 to 20 nm, preferably in the range of from 1 to 10 nm, more preferably in the range of from 2 nm to 8 nm, for example from 3 nm to 6 nm.

Supported copper catalyst used in accordance with the present invention have been found to be particularly advantageous as a selective di-olefin hydrogenation catalyst. Thus, in a further aspect, the present invention also provides a hydrogenation catalyst comprising copper supported on a carbon-containing support, wherein the surface-averaged particle size of the copper on the support is less than 10 nm.

It has been found that by incorporating the step of contacting the catalyst with a non-reducing atmosphere, preferably an oxygen-containing stream, and/or by varying the temperature of the reduction step, control of the size of the $Cu^0$ crystallites and particles at below 10 nm on the carbon-containing support may be achieved.

The hydrogenation catalyst produced as described above may be used to catalyse the hydrogenation of di-olefins in accordance with the process of the invention. As part of the process of the invention, a feed comprising one or more di-olefins is contacted with the supported catalyst in the presence of hydrogen and optionally also in the presence of one or more mono-olefins.

In some or all embodiments, the hydrogen may be supplied to the hydrogenation reaction in the gaseous phase. In some embodiments, hydrogen gas is supplied to the reaction alone or optionally in combination with one or more inert diluent gases. The inert gas may be helium, argon or nitrogen, preferably nitrogen. In some or all embodiments, the hydrogen may be dissolved and/or entrained in a suitable liquid solvent or the feed comprising the polyunsaturated hydrocarbon compound in the liquid phase, examples of suitable solvents include hydrocarbon solvents which are miscible with the polyunsaturated hydrocarbon compound.

The di-olefin, hydrogen and any optional mono-olefin that is present may be supplied to a reactor separately or preferably in combination in a single feed stream. Thus, in some preferred embodiments, a mixed feed stream is employed comprising hydrogen, di-olefin, optionally mono-olefin, and a balance of an inert diluent. In preferred embodiments, preferably wherein the mono-olefin is present in molar excess in comparison to the di-olefin. In preferred embodiments, the proportion of di-olefins in the feed relative to mono-olefins is less than 5% v/v, for example less than 1% v/v.

Prior to contacting the catalyst with the feed gas, the catalyst may be diluted with a non-catalytic material. This non-catalytic material may be any suitable material known in the art, for example, SiC. The catalyst and inert material may be mixed in any ratio which retains catalytic activity towards the hydrogenation of di-olefins, such as in the volume ratio of supported catalyst material:non-catalytic material of from 5:1 to 1:10, preferably 1:1 to 1:3.

Prior to contacting the catalyst with the feed, the catalyst may be reduced, or re-reduced if previously reduced and passivated by exposure to air, in order to activate the catalyst. This may be performed under the same conditions disclosed for reduction of the catalyst above. In embodiments, reduction is performed in hydrogen-containing gas at from 150 to 250° C. for 1 to 2 hours. Alternatively, the catalyst may be reductively activated in situ as a result of the presence of hydrogen in the feed stream to the reactor.

Contacting the supported catalyst with the reaction feed may be performed at any suitable temperature which affords a desired level of activity without negatively impacting upon reaction selectivity or risking reactant/product decomposition or significant amounts of unwanted by-product formation. Contacting the supported catalyst with the reaction feed may be performed in the gas phase, the liquid phase, or a mixed gas and liquid phase; if the supported catalyst is contacted with the reaction feed in the liquid phase, a suitable solvent may be present, for example a suitable hydrocarbon solvent. Suitably, a temperature of at least about 50° C. and less than about 300° C. may be employed. Preferably, the contacting step is performed at least about 80° C., more preferably at least about 100° C., even more preferably at least about 110° C. In other preferred embodiments, the contacting step is performed at a temperature of less than about 225° C., preferably less than about 200° C. The catalyst may be contacted with the reaction feed at any suitable pressure. In embodiments, the contacting step is performed at a pressure of about atmospheric pressure or above atmospheric pressure. In some embodiments, the contacting step is carried out at pressures of from 50 kPa absolute to 30,000 kPa absolute, from 100 kPa absolute to 10,000 kPa absolute, or from 250 kPa absolute to 5000 kPa absolute.

The temperature and pressures used during the contacting step may be introduced over a period in one or more ramping stages up to the desired temperature and pressure. This has not however been found to have a material benefit on reactant conversion or selectivity, thus suggesting that no significant changes in catalyst structure are induced under typical reaction conditions. By employing a carbon support, it has been found that a stable and inert catalyst may be produced that provides superior stability over time.

The catalysts of the present invention show superior di-olefin selectivity when compared to conventional copper on titania catalysts under the same reaction conditions. In particular, excellent reactant selectivity towards 1,3-butadiene in butylene has been found as one specific example, indicating that 1,3-butadiene is more strongly adsorbed onto the copper surface than butylene and other mono-olefins, thereby avoiding mono-olefin hydrogenation.

Alkynes containing a carbon-carbon triple bond are generally more reactive towards hydrogenation than di-olefins, as discussed for instance in M. Bender, *ChemBioEng Reviews* 2014, 1, 136-147. When one or more di-olefins are hydrogenated or are selectively removed from an excess of one or more mono-olefins, typically any alkynes present are also hydrogenated and hence removed. Therefore, the process of the present invention is also useful in the removal of alkynes, in addition to di-olefins, from a mono-olefin stream.

Thus, in another aspect, the present invention also provides the use of a catalyst as described herein comprising copper on a carbon-containing support to increase the selectivity towards di-olefin hydrogenation over mono-olefin hydrogenation in a process for hydrogenation of one or more di-olefins.

The performances of the catalysts of the present invention were tested over a prolonged time under reaction conditions. Remarkably, long-term stability was observed for the catalysts described herein, which is attributed to their resistance towards coking.

Thus, in another aspect, the present invention also provides the use of a catalyst as described herein comprising copper on a carbon-containing support to increase catalyst stability in a process for the hydrogenation of one or more di-olefins.

The invention will now be described by reference to the following non-limiting examples.

EXAMPLES

In the examples described hereinafter, analysis was performed using the following methods.

$N_2$ Physisorption $N_2$ physisorption isotherms were measured at −196° C. on a Micromeritics, TriStar 3000 V6.08 apparatus. Prior to the measurements, the samples were outgassed at 150° C., under dynamic vacuum for 14 h. The specific surface areas were calculated using multi-point Brunauer-Emmet-Teller (BET) analysis ($0.05<P/P_0<0.25$). The total pore volume was calculated as single point pore volume at $P/P_0$ of 0.99 and pore diameter distribution determined by Barrett-Joyner-Halenda (BJH) analysis applied to the adsorption branch.

TPR-TCD

Temperature programmed reduction (TPR) measurements on the final Cu/C catalysts were performed using a Micromeritics Autochem II ASAP 2920, equipped with a thermal conductivity detector (TCD). Prior to the measurements, the samples were dried at 120° C. for 0.5 h under Ar flow, before cooling down to room temperature. Next, the temperature was increased at 2° C. min$^{-1}$ to 400° C., in 5% $H_2$/Ar flow (1 mL min$^{-1}$ mg$_{cat}^{-1}$). During this step, the $H_2$ consumption was measured using the TCD and normalized to the amount of Cu in each sample.

The degree of reduction was calculated from the $H_2$ consumption by assuming the reduction stoichiometry: $Cu^{II}O+H_2 \rightarrow Cu^0+H_2O$. All catalyst could be completely reduced at 200° C.

XRD

Ex-situ x-ray diffraction was performed on a Bruker D8 powder X-ray diffractometer equipped with a Lynxeye detector. The used radiation was Co-Kα12 ($\lambda$=0.179026 nm), operated at 30 kV, 45 mA and a V20 variable slit. Diffractograms were taken first directly after the final reduction step in the synthesis. In the glovebox, a XRD specimen holder was loaded and subsequently sealed with an airtight transparent dome-like cap (A100B33, Bruker AXS), to collect diffractograms under Ar atmosphere. Diffractograms were typically collected at room temperature from 5-95 °2θ, with 0.1° increment and normalized to the intensity of the (002) diffraction of graphitic carbon at 30.9 °2θ. No background subtraction or smoothing was performed. Copper crystallite sizes were calculated using peak deconvolution software (Topas V5, Bruker AXS), applying the Scherrer equation with a shape factor k=0.1, to the $Cu^0$ (111) diffraction at (50.7 °2θ) and the $Cu^0$ (200) diffraction at (59.3 °2θ) (Patterson 1939).

TEM and HAADF-STEM

TEM imaging was performed on a Tecnai 20 (FEI) microscope and HAADF-STEM on a Talos F200X (FEI) microscope, both operated at 200 kV. To avoid electron beam induced particle growth, TEM images were acquired with a maximum electron dose-rate of ~5 electrons per nm$^2$ s$^{-1}$. TEM samples were prepared by grinding the catalyst into a fine powder, which was deposited directly onto a holey carbon coated copper TEM grid (Agar 300 mesh Cu). The surface-averaged particle size (PS) was determined by TEM analysis by measuring the size of at least 250 individual particles on different areas of the sample. The PS was calculated using: PS=√(($\Sigma_1^n D_i^2$)/($\Sigma_1^n$)), wherein $D_i$ is the diameter of the $i^{th}$ particle.

Gas Chromatography (GC)

The composition of the effluent gas mixture was analysed by on-line gas chromatography (GC). Data was acquired every 15 min using a flame ionization detector (Perichrom PR 2100, column filled with sebaconitrile 25% Chromosorb PAW 80/100 Mesh). GC peak areas were calibrated for butadiene, trans-2-butylene, cis-2-butylene, 1-butylene, n-butane, proyplene and propane using a pre-mixed calibration gas. The gas phase concentrations were calculated on the measured peak areas. To accurately quantify the hydrogenation of the mono-olefin propylene, the formation of propane was followed by GC. The butadiene reactant gas contained around 0.25% of cis-2-butylene trace impurity. The propylene reaction gas contained around 0.025% propane impurity. For these trace amounts, no significant influence on reaction kinetics is expected. For product analysis of these trace compounds, the initial concentration is subtracted from the measured value under reaction measurement. A blank measurement was performed to determine the fluctuations in butadiene flow and GC analysis. Herein, a standard deviation of ±1.1% butadiene was found. The GC detection limit was around 0.2 ppm for each analyte in the effluent gas, corresponding to <0.01% butane formation from butadiene.

Example 1—Oxidized Carbon Support

The catalysts were prepared using both pristine and modified high surface area graphite (HSAG) as support. The carbon supports consist mostly of graphite sheets, with a pore size distribution ranging from 2-50 nm. Pristine HSAG (P-HSAG) with a surface area of around 500 m$^2$ g$^{-1}$ and 0.7 mL g$^{-1}$ total pore volume was sourced from Timcal Ltd. The P-HSAG support was crushed and dried under dynamic vacuum at 170° C. for 1.5 h to remove absorbed water and finally stored in an Ar-filled glovebox until further use.

Optionally, the pristine HSAG support was pre-treated by liquid phase HNO$_3$ oxidation. 10 gram of HSAG was suspended in 400 mL of HNO$_{3(aq)}$ (68%), in a 1 L round bottom flask. The flask was equipped with a reflux cooler and heated using a heating mantle. The final temperature of 80° C. was reached after around 25 min and held then for 110 min. Subsequently, the reaction was quenched by diluting the suspension with cold deionized H$_2$O to around 2 L. The oxidized carbon material was allowed to sediment during 30 min, before decanting the mother liquid. The carbon was washed with deionized H$_2$O until reaching neutral pH, to remove residual HNO$_3$. After the final decantation, the carbon was collected in a beaker and dried overnight at 120° C. The resulting oxidized HSAG (Ox-HSAG) support was crushed and dried under dynamic vacuum at 170° C. for 1.5 h to remove absorbed water and finally stored in an Ar-filled glovebox until further use. The BET surface area was 426±2 m$^2$ g$^{-1}$, with a total pore volume of 0.62 mL g$^{-1}$.

Example 2—0.6 nm Cu/C Catalyst

A copper catalyst supported on a carbon-containing support (from here on referred to as Cu/C) with 0.6 nm Cu clusters was prepared, with a Cu loading of 2.7 wt %. Herein, around 2 g of the dried Ox-HSAG support of Example 1 was impregnated to incipient wetness in a round-bottom flask, under slight vacuum. An aqueous solution of Cu(NO$_3$)$_2$ in 0.1 M HNO$_3$, at pH of ~1 was used. The precursor solution was added by syringe. The Cu concentration was adjusted to obtain the desired Cu weight loading. The impregnate was stirred for 24 h to homogenize the Cu content. Next, the impregnate was dried overnight at room temperature, while stirred under dynamic vacuum. The dried impregnate was transferred to a plug-flow reactor and heated at 0.5° C. min$^{-1}$ to 230 and 1 h hold at 230° C. under N$_2$ flow (100 mL min$^{-1}$ g$^{-1}$), to decompose the nitrate precursor. The sample was cooled down and slowly exposed to air to obtain well-defined and high-dispersed Cu$^{II}$ species. 0.6 nm Cu$^0$ clusters were prepared in-situ by reduction inside the catalytic reactor at 200° C. An ex-situ reduction was performed on a sample under the same conditions to allow for XRD and HAADF-STEM analysis of the actual catalyst used in catalytic testing.

No copper crystallites could be observed by XRD under an argon atmosphere, after the ex-situ reduction treatment After passivation, no CuO or Cu$_2$O crystallites were observed by XRD. HHAADF-STEM was employed to determine the particle size, which was found to be 0.6±0.3 nm. Results of the various analyses, including an analysis of the copper particle dispersion, are provided in Table 1 below.

Example 3—3 nm Cu/C Catalyst

A Cu/C catalyst with 3 nm particle size was prepared with a Cu loading of 6.3 wt %. Herein, around 2 g of dried Ox-HSAG support of Example 1 was impregnated to incipient wetness in a round-bottom flask, under slight vacuum. An aqueous solution of Cu(NO$_3$)$_2$ in 0.1 M HNO$_3$, at pH of ~1 was used. The precursor solution was added by syringe. The Cu concentration was adjusted to obtain the desired Cu weight loading. The impregnate was stirred for 24 h to homogenize the metal content. Next, the impregnate was dried overnight at room temperature, while stirred under dynamic vacuum. The dried impregnate was transferred to a plug-flow reactor and heated at 0.5° C. min$^{-1}$ to 230° C. and 1 h hold at 230° C. under N$_2$ flow (100 mL min$^{-1}$ g$^{-1}$), to decompose the nitrate precursor. The sample was cooled down and treated with 20 vol % O$_2$/N$_2$ at room temperature to obtain well-defined and high-dispersed Cu$^{II}$ species. Then, the samples were flushed with N$_2$ for 30 min. After flushing, the samples were reduced by heating to 150° C. under 5 vol % H$_2$/N$_2$ flow (~1.5 mL min$^{-1}$ mg$_{cat}^{-1}$). The heating ramp was 2° C. min$^{-1}$, with 2 h hold at 150° C. Next, the temperature was increased at 2° C. min$^{-1}$ to 250° C. with 1 h hold, under the same atmosphere. After cooling down, the reduced sample was transferred in a closed vessel, to an Ar-filled glovebox (Mbraun Labmaster dp; <1 ppm H$_2$O; <1 ppm O$_2$).

Cu$^0$ crystallites of 2.0 nm were observed by XRD. TEM investigations showed 2.7±0.6 nm copper nanoparticles well-dispersed throughout the carbon. Results of the various analyses, including an analysis of the copper particle dispersion, are provided in Table 1 below.

Example 4—6 nm Cu/C Catalyst

A Cu/C catalysts with 6 nm particle size was prepared with a Cu loading of 6.3 wt %. Herein, around 2 g of dried Ox-HSAG support of Example 1 was impregnated to incipient wetness in a round-bottom flask, under slight vacuum. An aqueous solution of Cu(NO$_3$)$_2$ in 0.1 M HNO$_3$, at pH of ~1 was used. The precursor solution was added by syringe. The Cu concentration was adjusted to obtain the desired Cu weight loading. The impregnate was stirred for 24 h to homogenize the metal content. Next, the impregnate was dried overnight at room temperature, while stirred under dynamic vacuum. The dried impregnate was transferred to a plug-flow reactor and heated at 0.5° C. min$^{-1}$ to 230° C. and 1 h hold at 230° C. under N$_2$ flow (100 mL min$^{-1}$ g$^{-1}$), to decompose the nitrate precursor. The sample was cooled down and treated with 20 vol % O$_2$/N$_2$ at room temperature to obtain well-defined and high-dispersed Cu$^{II}$ species. Then, the samples were flushed with N$_2$ for 30 min. After flushing, the samples were reduced by heating to 150° C. under 5 vol % H$_2$/N$_2$ flow (~1.5 mL min$^{-1}$ mg$_{cat}^{-1}$). The heating ramp was 2° C. min$^{-1}$, with 2 h hold at 150° C. Next, the temperature was increased at 2° C. min$^{-1}$ to 400° C. with 1 h hold, under the same atmosphere. After cooling down, the reduced sample was transferred in a closed vessel, to an Ar-filled glovebox (Mbraun Labmaster dp; <1 ppm $H_2O$; <1 ppm $O_2$).

$Cu^0$ crystallites of 6.0 nm were observed by XRD. TEM investigations showed 6.3±2.0 nm copper nanoparticles well-dispersed throughout the carbon. Results of the various analyses, including an analysis of the copper particle dispersion, are provided in Table 1 below.

Example 5—13 nm Cu/C Catalyst

A Cu/C catalysts with 13 nm particle size was prepared with a Cu loading of 12.1 wt %. Herein, around 2 g of dried P-HSAG support of Example 1 was impregnated to incipient wetness in a round-bottom flask, under slight vacuum. An aqueous solution of $Cu(NO_3)_2$ in 0.1 M $HNO_3$, at pH of ~1 was used. The precursor solution was added by syringe. The Cu concentration was adjusted to obtain the desired Cu weight loading. The impregnate was stirred for 24 h to homogenize the metal content. Next, the impregnate was dried overnight at room temperature, while stirred under dynamic vacuum. The dried impregnate was transferred to a plug-flow reactor and heated at 2.0° C. $min^{-1}$ to 230° C. and 1 h hold at 230° C., under 20% $H_2/N_2$ flow (100 mL $min^{-1}$ $g^{-1}$). The sample was cooled down to room temperature and flushed with $N_2$ (100 mL $min^{-1}$ $g^{-1}$). Next, the catalyst was heated at 1° C. $min^{-1}$ to 200° C. with 3 h at this temperature, under 5% $O_2/N_2$ flow (100 mL $min^{-1}$ $g^{-1}$). At 200° C., the gas flow was exchanged for 15% $O_2/N_2$ flow (100 mL $min^{-1}$ $g^{-1}$) with 1 h hold, before cooling down to room temperature and collecting the final catalyst.

Moreover, an ex-situ reduction was done to allow for XRD and TEM analysis of the actual catalyst used for catalytic testing. Herein, the 13 nm Cu/C catalysts was loaded in a plug-flow reactor and heated at 2.0° C. $min^{-1}$ to 200° C. and 1 h hold at 200° C., under 20% $H_2/N_2$ flow (200 mL $min^{-1}$ $g^{-1}$). After cooling down, the reduced sample was transferred in a closed vessel, to an Ar-filled glovebox (Mbraun Labmaster dp; <1 ppm $H_2O$; <1 ppm $O_2$).

$Cu^0$ crystallites of 10.9 nm were observed by XRD. TEM investigations showed 12.9±4.8 nm copper nanoparticles well-dispersed throughout the carbon. Results of the various analyses, including an analysis of the copper particle dispersion, are provided in Table 1 below.

Example 6—19 nm Cu/C Catalyst

A Cu/C catalysts with 19 nm particle size was prepared with a Cu loading of 6.3 wt %. Herein, around 2 g of dried Ox-HSAG support of Example 1 was impregnated to incipient wetness in a round-bottom flask, under slight vacuum. An aqueous solution of $Cu(NO_3)_2$ in 0.1 M $HNO_3$, at pH of ~1 was used. The precursor solution was added by syringe. The Cu concentration was adjusted to obtain the desired Cu weight loading. The impregnate was stirred for 24 h to homogenize the metal content. Next, the impregnate was dried overnight at room temperature, while stirred under dynamic vacuum. The dried impregnate was transferred to a plug-flow reactor and heated at 0.5° C. $min^{-1}$ to 230° C. and 1 h hold at 230° C. under $N_2$ flow (100 mL $min^{-1}$ $g^{-1}$), to decompose the nitrate precursor. The sample was cooled down and treated with 20 vol % $O_2/N_2$ at room temperature to obtain well-defined and high-dispersed $Cu^{II}$ species. Then, the samples were flushed with $N_2$ for 30 min. After flushing, the samples were reduced by heating to 150° C. under 5 vol % $H_2/N_2$ flow (~1.5 mL $min^{-1}$ $mg_{cat}^{-1}$). The heating ramp was 2° C. $min^{-1}$, with 2 h hold at 150° C. Next, the temperature was increased at 2° C. $min^{-1}$ to 400° C. with 1 h hold, under the same atmosphere. Subsequently, the gas flow was changed to $N_2$ (100 mL $min^{-1}$ $g^{-1}$) and the temperature increased to 500° C. at 2° C. $min^{-1}$, with 1 h hold at 500° C. After cooling down, the reduced sample was transferred in a closed vessel, to an Ar-filled glovebox (Mbraun Labmaster dp; <1 ppm $H_2O$; <1 ppm $O_2$).

$Cu^0$ crystallites of 14.0 nm were observed by XRD. TEM investigations showed 19.4±6.9 nm copper nanoparticles well-dispersed throughout the carbon. Results of the various analyses, including an analysis of the copper particle dispersion, are provided in Table 1 below.

Comparative Example A

A copper catalyst supported on a titania-containing support (from here on referred to as $Cu/TiO_2$) with a Cu loading of 1.7 wt % was prepared. Herein, around 2 g of commercially available P25 $TiO_2$ (ex. Degussa) was impregnated to incipient wetness in a round-bottom flask, under slight vacuum. An aqueous solution of $Cu(NO_3)_2$ in 0.1 M $HNO_3$, at pH of ~1 was used. The precursor solution was added by syringe. The Cu concentration was adjusted to obtain the desired Cu weight loading. The impregnate was stirred for 24 h to homogenize the metal content. Next, the impregnate was dried overnight at room temperature, while stirred under dynamic vacuum. The dried impregnate was transferred to a plug-flow reactor and heated at 0.5° C. $min^{-1}$ to 250° C. and 1 h hold at 230° C. under $N_2$ flow (100 mL $min^{-1}$ $g^{-1}$), to decompose the nitrate precursor. The sample was cooled down and treated with 20 vol % $O_2/N_2$ at room temperature to obtain well-defined and high-dispersed $Cu^{II}$ species. Then, the samples were flushed with $N_2$ for 30 min. After flushing, the samples were reduced by heating to 150° C. under 5 vol % $H_2/N_2$ flow (~1.5 mL $min^{-1}$ $mg_{cat}^{-1}$). The heating ramp was 2° C. $min^{-1}$, with 2 h hold at 150° C. Next, the temperature was increased at 2° C. $min^{-1}$ to 250° C. with 1 h hold, under the same atmosphere. After cooling down, the reduced sample was transferred in a closed vessel, to an Ar-filled glovebox (Mbraun Labmaster dp; <1 ppm $H_2O$; <1 ppm $O_2$).

Comparative Example B

A $Cu/TiO_2$ catalyst with a Cu loading of 1.7 wt % was prepared. Herein, around 2 g of commercially available P25 $TiO_2$ (ex. Degussa) was impregnated to incipient wetness in a round-bottom flask, under slight vacuum. An aqueous solution of $Cu(NO_3)_2$ in 0.1 M $HNO_3$, at pH of ~1 was used. The precursor solution was added by syringe. The Cu concentration was adjusted to obtain the desired Cu weight loading. The impregnate was stirred for 24 h to homogenize the metal content. Next, the impregnate was dried overnight at room temperature, while stirred under dynamic vacuum. The dried impregnate was transferred to a plug-flow reactor and heated at 0.5° C. $min^{-1}$ to 250° C. and 1 h hold at 230° C. under $N_2$ flow (100 mL $min^{-1}$ $g^{-1}$), to decompose the nitrate precursor. The sample was cooled down and treated with 20 vol % $O_2/N_2$ at room temperature to obtain well-defined and high-dispersed $Cu^{II}$ species. Then, the samples were flushed with $N_2$ for 30 min. After flushing, the samples were reduced by heating to 150° C. under 5 vol % $H_2/N_2$ flow (~1.5 mL $min^{-1}$ $mg_{cat}^{-1}$). The heating ramp was 2° C. $min^{-1}$, with 2 h hold at 150° C. Next, the temperature was increased at 2° C. $min^{-1}$ to 400° C. with 1 h hold, under the same atmosphere. After cooling down, the reduced sample was transferred in a closed vessel, to an Ar-filled glovebox (Mbraun Labmaster dp; <1 ppm $H_2O$; <1 ppm $O_2$).

Comparative Example C

A gold catalyst supported on a carbon-containing support (from here on referred to as Au/C) with a Au loading of 1 wt % was prepared. First, an oxidized carbon nanotube support was prepared by liquid phase oxidation treatment. Herein, around 2 grams of commercial carbon nanotubes (ex. Baytubes) was suspended in 400 mL of $HNO_{3\ (aq)}$ (68%), in a 500 mL round bottom flask. The flask was equipped with a reflux cooler and heated using a heating mantle. The final temperature of 120° C. was held for 120 min. After cooling down, the oxidized carbon nanotube support was collected by filtration, washed thoroughly with deionized water and dried at 120° C. overnight.

Next, a deposition method using colloidal polyvinylpyrrolidone (PVP)-stabilized Au nanoparticles was used to prepare the Au/C catalyst. Herein, a freshly prepared solution of $NaBH_4$ in methanol was added to 5 mL of a solution containing PVP (molecular weight around 29,000) and $HAuCl_4.3H_2O$ in methanol. The amounts of reagents were adjusted to obtain a molar ratio of $NABH_4:PVP_{monomer}:Au$ precursor as 10:10:1. The resulting solution was stirred overnight to ensure complete decomposition of NaBH4. Next, colloidal nanoparticles were immobilized on the support by adding the colloid solution to the oxidized carbon nanotube support suspended in a small volume of methanol, under vigorous stirring. The amount of support material was adjusted to obtain 1 wt % metal loading. The solid was recovered by centrifugation and washed twice with methanol and diethyl ether, and subsequently dried at 60° C. overnight. PVP was removed from supported Au nanoparticles by washing the catalyst in an excess of Milli-Q water at room temperature overnight. The final catalyst was collected after drying.

$Au^0$ crystallites of 4.9 nm were observed by XRD. Results of the analyses are provided in Table 1 below.

Comparative Example D

A Au/C catalyst with Au loading of 4 wt % was prepared. First, a solution of $Au(en)_2Cl_3$ metal precursor was prepared. Herein, 0.449 mL of an aqueous solution of $HAuCl_4$ (17 wt % Au) containing 0.125 g (0.635 mmol) of Au was diluted to 2.5 mL in demineralized $H_2O$ in a glass beaker. To this solution, 0.15 mL (2.25 mmol) of pure ethylene diamine was added dropwise, while stirring at 400 RPM. The beaker was covered by parafilm and aluminium foil to avoid exposure to light. The system was left to react for 30 min while stirring at 400 RPM. Subsequently, 30 mL of absolute ethanol was added to the solution and a yellow/white precipitate formed. The suspension was left overnight to settle the solid. The following day, the liquid was decanted and the yellow gold precursor was left overnight to dry in the dark. The following day, the gold precursor was re-dissolved in demineralized $H_2O$ to a total volume of 2.5 mL and stored at 4° C. until further use.

Next, the gold precursor solution (1.88 mL) was dissolved in demineralized $H_2O$ to a total volume of 40 mL. While stirring at 400 RPM, 0.45 mL of a 1 M NaOH solution was added. Subsequently, 2 grams of dried Ox-HSAG from Example 1 was dispersed in the solution while stirring at 700 RPM and left the suspension stirring for 2 hours. Next, the solid was collected by repeated centrifugation (10 min at 4000 RPM) and decanting of the liquid, for three times. The solid was dried overnight at 60° C. and then under vacuum at room temperature for 24 hours. The Au/C catalyst was heated in a fluidized bed reactor, at 5° C. $min^{-1}$ to 400° C. for 2 hours under a flow of 20% $O_2/N_2$ (100 mL $min^{-1}$ $g^{-1}$). After cooling down, the final catalysts was collected and stored in the dark until further use.

$Au^0$ crystallites of 28.5 nm were observed by XRD. Results of the analyses are provided in Table 1 below.

TABLE 1

| Example | Cu loading (wt %) | Au loading (wt %) | Crystallite size (nm) | Particle size (nm) |
|---|---|---|---|---|
| 2 | 2.7 | — | <1 | 0.6 ± 0.3 |
| 3 | 6.3 | — | 2.0 | 2.7 ± 0.7 |
| 4 | 6.3 | — | 6.0 | 6.3 ± 2.0 |
| 5 | 12.1 | — | 10.9 | 12.9 ± 4.8 |
| 6 | 6.3 | — | 14.0 | 19.4 ± 6.9 |
| A | 1.7 | — | n.d. | n.d. |
| B | 1.7 | — | n.d. | n.d. |
| C | — | 1 | 28.5 | n.d. |
| D | — | 4 | 4.9 | n.d. |

Example 7—Granulate Formation

The passivated Cu/C catalysts of Examples 2-6 and Comparative Examples A-D were pelleted, ground and sieved to obtain a granulate size of 90-212 μm.

To corroborate that the reaction was not mass transfer limited, copper catalysts with different granulate size (38-90, 90-212 and 212-425 μm) were tested. No significant differences in the activity profiles for catalysts of different granulate size were observed, indicating that the reaction was not hindered by internal or external mass transfer limitations. A blank measurement was done, using only Ox-HSAG from Example 1, SiC and glass wool plugs. After the typical pre-treatment method, no butadiene or propylene consumption was observed up to 300° C.

Example 8—Catalyst Dilution, Reactor Loading and Reduction of the Catalyst

Catalytic hydrogenation tests were performed in a quartz plug flow reactor (4 mm internal diameter) at atmospheric pressure.

The catalyst samples from Examples 2-6 and Comparative Examples A-D were diluted with SiC (granulate size 212-425 um) as indicated in Table 2 below. The desired catalyst was then loaded directly into a fixed-bed quartz reactor, onto a glass frit. Small glass wool plugs were added before and after the catalyst bed, to ensure that the catalyst bed remained in place.

In-situ reduction of the catalyst was performed by heating the sample at 2° C. $min^{-1}$ to 200° C., with 120 min hold at 200° C. (50 mL $min^{-1}$ pure $H_2$) to obtain $Cu^0$.

TABLE 2

| Catalyst | Weight of Catalyst (mg) | Weight of SiC (mg) |
|---|---|---|
| Example 2 | 47.4 | 85 |
| Example 3 | 20.0 | 155 |
| Example 4 | 20.0 | 155 |
| Example 5 | 10.6 | 190 |
| Example 6 | 20.0 | 155 |
| Comparative Example A | 73.60 | 100 |

TABLE 2-continued

| Catalyst | Weight of Catalyst (mg) | Weight of SiC (mg) |
|---|---|---|
| Comparative Example B | 73.60 | 100 |
| Comparative Example C | 50.0 | 210 |
| Comparative Example D | 20.0 | 200 |

Example 9—Catalyst Activity

The conversion of butadiene and propylene in a 1% butadiene in propylene feed composition for the catalyst loaded and reduced as described in Example 8 were studied at a reaction temperature of 30° C. to 195° C. The gas hourly space velocity (GHSV) of the gas feed was around 90,000 $h^{-1}$. The feed gas had a composition of butadiene/proyplene/$H_2$/He=0.15/15/10/24.85 mL $min^{-1}$ with a total flow of 50 mL $min^{-1}$.

The results for butadiene and propylene conversion at 120° C. and 150° C. are presented in Table 3 below.

TABLE 3

| | Conversions (%) at 120° C. | | Conversions (%) at 150° C. | |
|---|---|---|---|---|
| Example | Butadiene | Propylene | Butadiene | Propylene |
| 2 | 35.99 | 0.00 | 96.44 | 0.01 |
| 3 | 99.76 | 0.01 | 100.00 | 0.05 |
| 4 | 100.00 | 0.02 | 100.00 | 0.03 |
| 5 | 0.61 | 0.00 | 100.00 | 0.02 |
| 6 | 0.00 | 0.00 | 11.01 | 0.01 |
| A | 0.00 | 0.00 | 1.42 | 0.00 |
| B | 0.00 | 0.00 | 3.88 | 0.02 |
| C | 5.33 | 0.00 | 2.14 | 0.00 |
| D | 0.48 | 0.00 | 1.03 | 0.00 |

Example 10—Catalyst Activity—Temperature Ramping Experiments

Reactant conversion for di-olefins and mono-olefins of the catalysts loaded and reduced as described in Example 8 were studied as a function of temperature over a continuous temperature ramping experiment. For continuous temperature ramping experiments, the catalysts were cooled down to 30° C. under $H_2$ flow, directly after the in-situ reduction and the sample exposed to the pre-mixed reaction gas feed containing 1,3-butadiene/propylene/$H_2$/He in a ratio of 0.15/15/10/24.85 mL $min^{-1}$ at 1 bar. For the catalysts of Examples 2 to 6, the reactor was heated at 0.5° C. $min^{-1}$ to 195° C., cooled down to 30° C. and again heated to 195° C. at the same rate and atmosphere, for the catalysts of Comparative Examples A to D, the maximum heating temperature was greater than 195° C. During the temperature ramping, data was acquired every 7.5° C. After the ramp, the catalyst was cooled down and passivated at room temperature by slowly exposing it to air.

The results for Examples 2-6 and Comparative Examples A-D are provided in Tables 4-12. In Tables 4-7 presented below, the butadiene conversion remained at 100% as measured at temperatures greater than the highest indicated temperature in the respective table.

TABLE 4

Catalyst from Example 2

| Temperature (° C.) | Butadiene conversion (%) | Propylene conversion (%) |
|---|---|---|
| 83 | 0.00 | 0.00 |
| 90 | 0.42 | 0.00 |
| 98 | 1.05 | 0.00 |
| 105 | 1.03 | 0.00 |
| 113 | 5.22 | 0.00 |
| 120 | 35.99 | 0.00 |
| 127 | 69.66 | 0.00 |
| 135 | 84.45 | 0.00 |
| 143 | 92.27 | 0.01 |
| 150 | 96.44 | 0.01 |
| 158 | 98.55 | 0.01 |
| 165 | 99.55 | 0.01 |
| 172 | 99.86 | 0.01 |
| 180 | 100.00 | 0.02 |

TABLE 5

Catalyst from Example 3

| Temperature (° C.) | Butadiene conversion (%) | Propylene conversion (%) |
|---|---|---|
| 90 | 0.00 | 0.00 |
| 98 | 0.46 | 0.00 |
| 105 | 0.64 | 0.00 |
| 113 | 57.96 | 0.00 |
| 120 | 99.76 | 0.01 |
| 128 | 100.00 | 0.03 |

TABLE 6

Catalyst from Example 4

| Temperature (° C.) | Butadiene conversion (%) | Propylene conversion (%) |
|---|---|---|
| 90 | 0.00 | 0.00 |
| 98 | 0.07 | 0.00 |
| 105 | 17.86 | 0.00 |
| 113 | 86.22 | 0.01 |
| 120 | 100.00 | 0.02 |

TABLE 7

Catalyst from Example 5

| Temperature (° C.) | Butadiene conversion (%) | Propylene conversion (%) |
|---|---|---|
| 97 | 0.00 | 0.00 |
| 105 | 0.40 | 0.00 |
| 113 | 0.59 | 0.00 |
| 120 | 0.61 | 0.00 |
| 127 | 0.76 | 0.00 |
| 135 | 43.45 | 0.00 |
| 143 | 92.90 | 0.01 |
| 150 | 100.00 | 0.02 |

TABLE 8

Catalyst from Example 6

| Temperature (° C.) | Butadiene conversion (%) | Propylene conversion (%) |
|---|---|---|
| 127 | 0.00 | 0.00 |
| 135 | 1.84 | 0.00 |
| 143 | 5.11 | 0.00 |
| 150 | 11.01 | 0.01 |
| 158 | 20.20 | 0.01 |
| 165 | 30.77 | 0.01 |

TABLE 8-continued

Catalyst from Example 6

| Temperature (° C.) | Butadiene conversion (%) | Propylene conversion (%) |
|---|---|---|
| 172 | 42.20 | 0.01 |
| 180 | 53.10 | 0.01 |
| 187 | 63.49 | 0.02 |
| 195 | 72.32 | 0.02 |

TABLE 9

Catalyst from Comparative Example A

| Temperature (° C.) | Butadiene conversion (%) | Propylene conversion (%) |
|---|---|---|
| 143 | 0.00 | 0.00 |
| 150 | 1.42 | 0.00 |
| 158 | 1.59 | 0.00 |
| 165 | 1.73 | 0.00 |
| 173 | 2.82 | 0.00 |
| 180 | 2.45 | 0.00 |
| 188 | 3.27 | 0.00 |
| 195 | 3.17 | 0.00 |
| 203 | 3.51 | 0.00 |
| 210 | 5.02 | 0.00 |
| 218 | 6.15 | 0.00 |
| 225 | 9.11 | 0.00 |
| 233 | 13.73 | 0.00 |
| 240 | 18.94 | 0.00 |
| 248 | 28.94 | 0.00 |
| 255 | 40.77 | 0.00 |
| 263 | 60.37 | 0.00 |
| 270 | 79.09 | 0.00 |
| 278 | 86.85 | 0.01 |
| 285 | 86.20 | 0.01 |

TABLE 10

Catalyst from Comparative Example B

| Temperature (° C.) | Butadiene conversion (%) | Propylene conversion (%) |
|---|---|---|
| 128 | 0.00 | 0.01 |
| 135 | 1.24 | 0.01 |
| 143 | 3.24 | 0.01 |
| 150 | 3.88 | 0.02 |
| 158 | 4.49 | 0.02 |
| 165 | 5.54 | 0.02 |
| 173 | 6.96 | 0.03 |
| 180 | 8.39 | 0.03 |
| 188 | 9.68 | 0.03 |
| 195 | 12.59 | 0.03 |
| 203 | 15.64 | 0.03 |
| 210 | 20.77 | 0.03 |
| 218 | 28.86 | 0.03 |
| 225 | 39.02 | 0.02 |
| 233 | 55.34 | 0.02 |
| 240 | 77.16 | 0.02 |
| 248 | 97.18 | 0.02 |
| 255 | 99.97 | 0.03 |
| 263 | 100.00 | 0.03 |

TABLE 11

Catalyst from Comparative Example C

| Temperature (° C.) | Butadiene conversion (%) | Propylene conversion (%) |
|---|---|---|
| 30 | 3.38 | 0.00 |
| 38 | 1.95 | 0.00 |
| 45 | 1.36 | 0.00 |
| 53 | 2.09 | 0.00 |
| 60 | 1.21 | 0.00 |
| 68 | 0.79 | 0.00 |
| 75 | 1.55 | 0.00 |
| 83 | 2.93 | 0.00 |
| 90 | 3.40 | 0.00 |
| 98 | 2.75 | 0.00 |
| 105 | 1.76 | 0.00 |
| 113 | 2.87 | 0.00 |
| 120 | 5.33 | 0.00 |
| 128 | 3.62 | 0.00 |
| 135 | 4.46 | 0.00 |
| 143 | 2.64 | 0.00 |
| 150 | 2.14 | 0.00 |
| 158 | 2.64 | 0.00 |
| 165 | 4.17 | 0.00 |
| 173 | 3.12 | 0.00 |
| 180 | 7.23 | 0.01 |
| 188 | 8.45 | 0.01 |
| 195 | 9.54 | 0.01 |
| 203 | 9.52 | 0.01 |
| 210 | 13.29 | 0.01 |
| 218 | 13.32 | 0.01 |
| 225 | 17.52 | 0.01 |
| 233 | 17.31 | 0.01 |
| 240 | 21.83 | 0.01 |
| 248 | 19.39 | 0.01 |
| 255 | 21.42 | 0.00 |
| 263 | 19.26 | 0.00 |
| 270 | 21.01 | 0.00 |
| 278 | 18.47 | 0.00 |
| 285 | 18.72 | 0.00 |
| 293 | 17.74 | 0.00 |
| 300 | 15.76 | 0.00 |

TABLE 12

Catalyst from Comparative Example D

| Temperature (° C.) | Butadiene conversion (%) | Propylene conversion (%) |
|---|---|---|
| 98 | 0.00 | 0.00 |
| 105 | 0.04 | 0.00 |
| 113 | 0.13 | 0.00 |
| 120 | 0.48 | 0.00 |
| 128 | 0.81 | 0.00 |
| 135 | 0.81 | 0.00 |
| 143 | 0.34 | 0.00 |
| 150 | 1.03 | 0.00 |
| 158 | 1.01 | 0.00 |
| 165 | 1.29 | 0.00 |
| 173 | 1.41 | 0.00 |
| 180 | 1.89 | 0.00 |
| 188 | 2.30 | 0.00 |
| 195 | 2.80 | 0.00 |
| 203 | 3.47 | 0.00 |
| 210 | 3.89 | 0.00 |
| 218 | 4.33 | 0.00 |
| 225 | 4.98 | 0.00 |
| 233 | 5.38 | 0.00 |
| 240 | 5.50 | 0.00 |
| 248 | 5.80 | 0.00 |
| 255 | 6.11 | 0.00 |
| 263 | 6.08 | 0.00 |
| 270 | 5.84 | 0.00 |
| 278 | 5.21 | 0.00 |
| 285 | 0.00 | 0.00 |
| 293 | 0.11 | 0.00 |
| 300 | 0.35 | 0.00 |

As can clearly be seen from Tables 5 and 6, above 120° C. effectively all of the butadiene was completely removed by the catalysts of Example 3 and 4, whilst the conversion of propylene was remarkably low, only ~0.01-0.02% propylene was hydrogenated, even though propylene was supplied in 100-fold excess of 1,3-butadiene.

Example 11—Stability Testing

The catalysts of Examples 3 and 4 which were studied as a function of time over an isothermal experiment. For the isothermal experiment, the Cu/C catalyst from used in Example 3 and Example 4 were cooled down to 80° C. under $H_2$ flow, after in-situ reduction. Then, the catalysts were exposed to the reaction feed gas containing 1,3-butadiene/propylene/$H_2$/He in a ratio of 0.15/15/10/24.85 mL min$^{-1}$. The catalysts were then heated at 2° C. min$^{-1}$ to 110° C. at 1 bar. Upon reaching the final temperature of 110° C., the reaction time was determined as $t_0$. The catalyst was held at 110° C. for at least 100 h on stream, before cooling down and passivating the sample at room temperature by slowly exposing it to air. The results are presented in Tables 13 and 14 below.

TABLE 13

Catalyst from Example 3

| Time on stream (h) | Butadiene conversion (%) | Propylene conversion (%) | Cu time yield (mmol$_{butadiene}$ s$^{-1}$ gram$_{Cu}^{-1}$) |
|---|---|---|---|
| 0 | 90.80 | 0.01 | 82.29 |
| 10 | 53.47 | 0.00 | 48.46 |
| 20 | 49.22 | 0.00 | 44.60 |
| 30 | 46.37 | 0.00 | 42.03 |
| 40 | 47.00 | 0.00 | 42.59 |
| 50 | 47.07 | 0.00 | 42.66 |
| 60 | 48.98 | 0.00 | 44.39 |
| 70 | 46.95 | 0.00 | 42.55 |
| 80 | 48.18 | 0.00 | 43.66 |
| 90 | 48.22 | 0.00 | 43.70 |
| 100 | 48.01 | 0.00 | 43.51 |

TABLE 14

Catalyst from Example 4

| Time on stream (h) | Butadiene conversion (%) | Propylene conversion (%) | Cu time yield (mmol$_{butadiene}$ s$^{-1}$ gram$_{Cu}^{-1}$) |
|---|---|---|---|
| 0 | 99.54 | 0.04 | 90.21 |
| 10 | 89.72 | 0.01 | 81.31 |
| 20 | 87.16 | 0.01 | 78.99 |
| 30 | 85.25 | 0.00 | 77.25 |
| 40 | 84.43 | 0.00 | 76.51 |
| 50 | 84.42 | 0.00 | 76.51 |
| 60 | 84.14 | 0.00 | 76.25 |
| 70 | 82.94 | 0.00 | 75.16 |
| 80 | 82.58 | 0.00 | 74.84 |
| 90 | 81.90 | 0.00 | 74.22 |
| 100 | 79.71 | 0.00 | 72.24 |

During the first hours on stream, the catalysts showed higher conversion than in the temperature ramping experiments at 110° C. This activation is likely due to changes in catalyst structure, which were not apparent during the temperature ramping experiments. The conversions decrease most rapidly in the first 20 h on stream and then showed a significantly slower rate of decrease of conversion.

A cause for change in activity for supported metal nanoparticles, as observed in the stability tests, could be particle growth. Therefore, the spent catalysts were analysed after 100 h on stream. The samples of catalyst from Example 3 grew to 4.7±2.1 nm, whereas the samples of catalyst from Example 4 grew only slightly, to 6.5±1.9 nm.

The invention claimed is:

1. A process for the hydrogenation of polyunsaturated hydrocarbon compounds, said process comprising contacting a feed comprising at least one di-olefin in the presence of hydrogen with a catalyst comprising copper on a carbon-containing support material, wherein the hydrogenation selectively hydrogenates the at least one di-olefin over a corresponding mono-olefin.

2. The process according to claim 1, wherein the carbon-containing support material is a carbon-based support material.

3. The process according to claim 2, wherein the carbon-based support material is selected from graphite, graphene, carbon aerogels, carbon nanotubes and carbon nanofibers and carbon nanoplatelets, polymeric materials, carbon black, turbostratic carbon and activated carbon.

4. The process according to claim 1, wherein the catalyst additionally comprises one or more metallic promoters or modifiers selected from silver, gold, potassium, sodium, zinc, manganese, chromium or mixtures thereof, either in their metallic form or in the form of oxides.

5. The process according to claim 1, wherein the catalyst comprises copper in an amount of from 1 to 15 wt. % based on the total weight of the catalyst.

6. The process according to claim 1, wherein the feed further comprises at least one mono-olefin.

7. The process according to claim 1, wherein the proportion of di-olefins in the feed relative to mono-olefins is less than 5% v/v.

8. The process according to claim 1, wherein the feed further comprises at least one alkyne.

9. The process according to claim 1, wherein the feed comprises butene, butadiene and optionally butyne.

10. The process according to claim 1, wherein the contacting step is performed at a temperature of at least 50° C. and less than 300° C.

11. The process according to claim 1, wherein the contacting step is performed at a pressure which is at or above atmospheric pressure.

12. The process according to claim 1, wherein the surface-averaged particle size of copper particles on the carbon-containing support material is in a range of from 0.5 to 20 nm.

* * * * *